(12) United States Patent
Park et al.

(10) Patent No.: US 7,635,589 B2
(45) Date of Patent: Dec. 22, 2009

(54) METHOD FOR THE PREPARATION OF A DERMAL PAPILLA TISSUE HAVING HAIR FOLLICLE INDUCTIVE POTENCY

(75) Inventors: Jung-Keug Park, Munchon 4-danji Samick Apt. 406-201, Juyeop-2-dong, Ilsan-gu, Goyang-si (KR) 411-747; Doo-Hoon Lee, Seoul (KR); Hee-Hoon Yoon, Incheon (KR); Youn-Ho Shin, Daejeon (KR); Young Jin Kim, Seoul (KR)

(73) Assignees: Lifecord Inc., Corp., Seoul (KR); Jung-Keug Park, Goyang-si (KR)

( * ) Notice: Subject to any disclaimer, the term of this patent is extended or adjusted under 35 U.S.C. 154(b) by 221 days.

(21) Appl. No.: 11/720,217

(22) PCT Filed: Nov. 29, 2005

(86) PCT No.: PCT/KR2005/004040

§ 371 (c)(1),
(2), (4) Date: May 25, 2007

(87) PCT Pub. No.: WO2006/057542

PCT Pub. Date: Jun. 1, 2006

(65) Prior Publication Data

US 2008/0145929 A1 Jun. 19, 2008

(30) Foreign Application Priority Data

Nov. 29, 2004 (KR) .................... 10-2004-0098680

(51) Int. Cl.
*C12N 5/06* (2006.01)
(52) U.S. Cl. ................... 435/325; 435/377; 435/404; 435/406; 435/407
(58) Field of Classification Search ................. None
See application file for complete search history.

(56) References Cited

U.S. PATENT DOCUMENTS 5,851,831 A  12/1998 Inamatsu et al.

FOREIGN PATENT DOCUMENTS

| WO | WO 95/01423 A1 | 1/1995 |
| WO | WO 03/022043 A1 | 3/2003 |
| WO | WO 03/051419 A1 | 6/2003 |
| WO | WO 03/052085 A1 | 6/2003 |

OTHER PUBLICATIONS

Inamatsu et al., Journal of Investigation Dermatology Nov. 1998;111(5):767-775.*

* cited by examiner

*Primary Examiner*—Daniel C Gamett
(74) *Attorney, Agent, or Firm*—Sughrue Mion, PLLC

(57) ABSTRACT

The inventive method for the preparation of a dermal papilla tissue in accordance with the present invention makes it possible to form a quantity of the dermal papilla tissues having hair follicle inductive ability, and accordingly, it can be effectively used for the treatment of alopecia through cell transplantation.

7 Claims, 7 Drawing Sheets

A

B

D

C

E

F

Dermal papilla cell     Lower dermal sheath cell

METHOD FOR THE PREPARATION OF A DERMAL PAPILLA TISSUE HAVING HAIR FOLLICLE INDUCTIVE POTENCY

This is a national stage application under 35 U.S.C. §317 of PCT/KR2005/004040 filed on Nov. 29, 2005, which claims priority from Korean patent application 10-2004-0098680 filed on Nov. 29, 2004, all of which are incorporated herein reference.

FIELD OF THE INVENTION

The present invention relates to a method for preparing a dermal papilla tissue having hair follicle inductive potency which comprises the steps of proliferating dermal papilla and lower dermal sheath cells isolated from the hair follicle in a primary culture medium known in the art, and culturing the proliferated cells in a secondary culture medium supplemented with high concentrations of amino acids, vitamins and a growth factor.

BACKGROUND OF THE INVENTION

It is believed that alopecia (baldness) is hereditary and occurs when the hair follicles slowly begin to produce finer and shorter hairs, or stop producing hairs at all. There are many forms of hair loss, ranging from alopecia areata to androgenic alopecia, also known as male or female pattern baldness.

In the past, alopecia was typically treated by various methods of implanting synthetic or artificial hair into hair follicle root bulbs of the scalp, but such artificial hair implant methods have been almost always ineffective, often leading to patient health problem and further natural hair follicle loss. Currently, there are two methods employed to treat alopecia: drug therapy and human hair transplantation. The drug therapy may enhance the hair growth and prevent future hair loss, but it is associated with problems such as skin irritation and accelerated hair loss where the medication is stopped after a prolonged use. The transplantation of human hair, on the other hand, involves taking plugs of natural hair from hair growing areas and transplanting them to bald areas. The transplanted hair settles at the transplant area as a complete hair follicle and becomes a permanent hair that undergoes a normal growth cycle. However, the number of hair to be transplanted is very limited, and in case of transplanting about 2,000 hairs per one operation, it is not plausible to perform more than three such operations. Further, it is a tedious and expensive procedure that requires the expertise of a skilled physician and the motivation and tolerance of the patient. This treatment is usually not performed for females with androgenetic alopecia, since the loss of hair is too diffuse.

Thus, the currently used methods of treatment for alopecia have numerous limitations, and therefore, there have been reported many studies to overcome such problems through culturing hair follicle forming cells in vitro and implanting them.

Arase et al. have disclosed that when plucked follicles are cultured in vitro together with isolated dermal papilla cells, the hair follicle cells move toward the dermal papilla and form new hair bulbs (Arase S. et al., *Skin Pharmacol.* 7(1-2):12-5, 1994), which suggests that the formation and maintenance of the hair follicle are achieved by complex and intimate interactions between the outer root sheath (ORS) cells and dermal papilla cells, and if such interactions are reproduced, it is possible to re-constitute the hair follicle. Further, Cohen and Oliver have shown that dermal papilla cells play a key role in the growth of the hair follicle (Cohen J., *J Embryol Exp Morphol.* 9:117-27, 1961; Oliver RF., *J Embryol Exp Morphol.* 15(3):331-47, 1966; and Oliver R F., *J Embryol Exp Morphol.* 18(1):43-51, 1967).

Reynolds et al. have reported that when dermal papilla cells are isolated and cultured in vitro, the dermal papilla cells gradually lose their innate hair follicle-inductive potency after about 3 to 4 passage numbers (Reynolds A J et al., *Development* 122 (10):3085-94, 1996), while Inamatsu et al. have found that when rat's hair follicle dermal forming cells are cultured in a waste medium of epithelial cells, the dermal papilla cells retain their hair follicle-inductive ability (Inamatsu M. et al., *J Invest Dermatol.* 111(5):767-75, 1998).

Jahoda and Reynolds have reported that as a result of isolating and culturing the dermal papilla cells of rat's vibrissa hair and implanting the cultured cells of 3 passage numbers or less into small ear skin wounds and the back of rats, abnormally large hair fibers displaying vibrissa hair-type characteristics emerge from the transplant sites (Jahoda C A., *Development.* 115(4):1103-9, 1992; and Reynolds A J. et al., *Development.* 115(2):587-93, 1992), and Gharzi et al. have disclosed that when the outer root sheath and lower dermal sheath of rat vibrissa hair are cultured in a collagen gel matrix which is similar to the real skin, inserted the real dermal papilla between these two cell layers, and transplanted it at the back of rat, the formation of the dermal papilla can be induced (Gharzi A. et al., *J Exp Dermatol.* 12(2):126-36, 2003). Further, Kevin et al. have demonstrated that the lower dermal sheath cells encompassing the dermal papilla as well as the dermal papilla cells have the hair follicle inductive ability (Kevin J. et al., *J Invest Dermatol.* 121: 1267-1275, 2003). Recently, the lower dermal sheath cells have been actively employed in the study for the formation of the hair follicle.

The present inventors have developed an effective method for in vitro re-constitution of a dermal papilla tissue important for the growth and maintenance of the hair follicle, which comprises the steps of proliferating dermal papilla and lower dermal sheath cells isolated from the hair follicle having hair follicle inductive potency in a primary culture medium well-known in the art, and culturing the proliferated cells in a secondary culture medium containing high concentrations of amino acids and vitamins together with a growth factor. The method of the present invention makes it possible to form a quantity of dermal papilla tissues through cell auto-aggregation without the use of any matrix or substrate.

SUMMARY OF THE INVENTION

Accordingly, it is an object of the present invention to provide a method for the in vitro preparation of a dermal papilla tissue for the purpose of forming a quantity of the dermal papilla tissues by cell auto-aggregation without the use of any matrix or substrate.

In accordance with one aspect of the present invention, there is provided a method for the preparation of a dermal papilla tissue which comprises the steps of:

1) isolating dermal papilla and lower dermal sheath cells from the hair follicle;

2) culturing the isolated cells in a primary culture medium up to 5 to 6 passage numbers, the primary culture medium containing 600 to 1,900 mg/l of amino acids and 12 to 36 mg/l of vitamins;

3) inducing auto-aggregation of the cells obtained in step (2) by culturing them in a secondary culture medium containing 2,000 to 3,000 mg/l of amino acids and 40 to 60 mg/l of vitamins, wherein the secondary culture medium is free of serum and is supplemented with 0.1 to 10,000 ng/ml of a growth factor; and 4) harvesting the auto-aggregated cells obtained in step (3) by centrifugation and culturing them in the culture medium of step (3).

BRIEF DESCRIPTION OF THE DRAWINGS

The above and other objects and features of the present invention will become apparent from the following description of the invention; when taken in conjunction with the accompanying drawings, which respectively show.

DETAILED DESCRIPTION OF THE INVENTION

Figure 1:
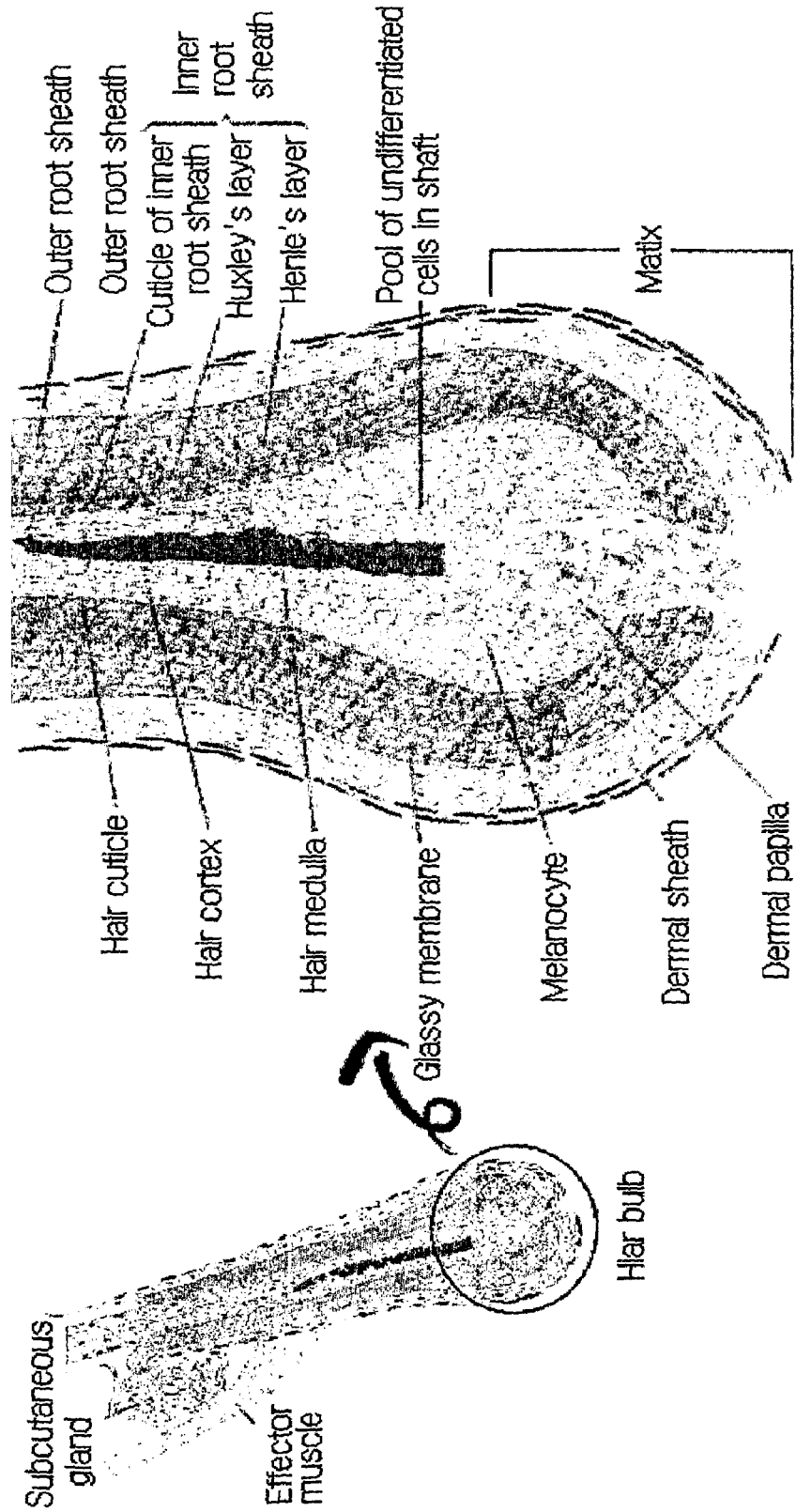
FIG. 1: the structure of the hair follicle.

In culturing dermal papilla and lower dermal sheath cells of the hair follicle, the preparation method of the present invention is characterized by culturing the dermal papilla and lower dermal sheath cells in a conventional culture medium (primary culture medium) containing 600 to 1,900 mg/l of amino acids and 12 to 36 mg/l of vitamins, and culturing the primary cultured cells in a high concentration serum-free medium (secondary culture medium) containing 2,000 to 3,000 mg/l of amino acids and 40 to 60 Mg/l of vitamins which is supplemented with 0.1 to 10,000 ng/ml of a growth factor.

The secondary culture medium of the present invention differs from the conventional culture medium in that 1) it does not contain any serum; 2) it contains 2 to 5-fold higher concentration of amino acids and vitamins; and 3) it further comprises a growth factor which is required for the growth and maintenance of the hair follicle.

In the method of the present invention, the dermal papilla and lower dermal sheath cells are separated from the fully grown hair follicle and subjected to a primary culture in a common cell culture medium according to a conventional method in the art. The cell culture medium used for the primary culture in the present invention may be selected, but are not limited to, from the group consisting of DMEM (Dulbecco's Modified Eagle's Medium), DMEM/F-12, F-12, McCoy's 5A, RPMI1640, Williams' medium E, IMDM (Iscove's Modified Dulbecco's Medium) and so on. The dermal-forming cells (dermal papilla and lower dermal sheath cells) can be proliferated through a series of the primary culture up to 5 to 6 passage numbers until the cells are judged to have lost their hair follicle inductive ability. The primary cultured cells are then cultured in the secondary culture medium which is a high concentration culture medium containing 2 to 5-fold higher concentrations of amino acids and vitamins than a common culture medium, together with a supplemented growth factor, without the use of any matrix or substrate. As a result, about 80% of the monolayer cultured cells thus prepared form auto-aggregates capable of reproducing the characteristics of dermal-forming cells. For example, in case of inoculating $1 \times 10^6$ cells at a 25 $cm^2$ culture dish, hundreds of auto-aggregates are formed.

Since the secondary culture medium used in the present invention contains 2 to 5-fold higher amino acids and vitamins than the common culture medium mentioned above, it can overcome the problem of depleted nutrients and oxygen during the culture of dermal papilla and lower dermal sheath cells, improving the differential characteristics of the cells, which results in helping the formation of a dermal papilla tissue.

Preferably, the secondary culture medium according to the present invention contains high concentrations of amino acids as follows: 30 to 200 mg/l each of L-arginine, L-asparagine, L-aspartic acid, L-cystine-2HCl, L-isoleucine, L-leucine, and L-lysine; 30 to 210 mg/l each of L-phenylalanine, L-tryptophan, and L-tyrosine; and 50 to 600 mg/l each of the rest of the essential amino acids.

Further, it is preferable for the secondary culture medium of the present invention to contain high concentrations of vitamins as follows: 0.02 to 1 mg/l each of biotin, D-Ca pantothenate and riboflavin as a soluble vitamin B; 3 to 16 mg/l each of choline chloride, folic acid, niacinamide, pyridoxine-HCl, and thiamine HCl; 10 to 15 mg/l of i-inositol; and 0.02 to 0.03 mg/l of vitamin $B_{12}$. More preferably, the medium of the present invention further comprises 0.03 to 0.07 mg/l of glutathione, 400 to 600 mg/l of glutamine, and 1,500 to 3,000 mg/l of D-glucose.

Further, more preferably, the secondary culture medium of the present invention comprises 3,000 to 3,500 mg/l of sodium bicarbonate ($NaHCO_3$) and 2,000 to 2,500 mg/l of HEPES (N-[2-hydroxyethyl]piperazine-N'-[2-ethanesulfonic acid]) having pH buffering effect; 1.0 to 2.0 mM of Ca and 0.5 to 1.0 mM of Mg that are trace elements essential for cell-cell adhesion; 0.25 to 0.7 nM each of Cu, Fe, Mn, and Zn, trace elements essential for cellular metabolism; and 4,000 to 5,000 mg/l of sodium chloride to adjust osmotic pressure at 280 to 310 mOsm/kg.

Furthermore, for the purpose of prolonging the culture period of the hair follicle, the secondary culture medium of the present invention further comprises hydrocortisone (HC), insulin (I), transferrin (T), and sodium selenite (S). For example, it is preferable for the secondary culture medium to contain 10 to 100 μg/l of hydrocortisone, 5 to 20 mg/l of insulin, 5 to 20 mg/l of transferrin, and 0.005 to 0.02 mg/l of sodium selenite.

In particular, it is more preferable to use a secondary culture medium comprising 165 mg/l of $CaCl_2$, 0.0001 mg/l of $CuSO_4.5H_2O$, 0.0001 mg/l of $Fe(NO_3).9H_2O$, 330 mg/l of KCl, 0.076 mg/l of $KNO_3$, 98 mg/l of $MgSO_4$, 0.0001 mg/l of $MnCl_2.4H_2O$, 4,800 mg/l of NaCl, 3,360 mg/l of $NaHCO_3$, 111 mg/l of $Na_2HPO_4$, 0.0002 mg/l of $ZnSO_4.7H_2O$, 2,000 mg/l of D-glucose, 110 mg/l of sodium pyruvate, 2,383 mg/l of HEPES, 15 mg/l of phenol red, 50 mg/l of L-alanine, 100 mg/l of L-arginine, 50 mg/l of L-asparagine, 60 mg/l of L-aspartic acid, 182.4 mg/l of L-cystine-2HCl, 150 mg/l of L-glutamic acid, 584 mg/l of L-glutamine, 60 mg/l of L-glycine, 62.1 mg/l of L-histidine, 210 mg/l of L-isoleucine, 210 mg/l of L-leucine, 292 mg/l of L-lysine-HCl, 60 mg/l of L-methionine, 132 mg/l of L-phenylalanine, 80 mg/l of L-proline, 84 mg/l of L-serine, 190 mg/l of L-threonine, 32 mg/l of L-tryptophan, 208 mg/l of L-tyrosine, 188 mg/l of L-valine, 0.026 mg/l of biotin, 0.026 mg/l of D-Ca pantothenate, 8 mg/l of choline chloride, 16 mg/l of folic acid, 14.40 mg/l of i-inositol, 8 mg/l of niacinamide, 8 mg/l of pyridoxine.HCl, 0.8 mg/l of riboflavin, 3 mg/l of thiamine.HCl, and 0.026 mg/l of vitamin $B_{12}$.

The secondary culture medium preferably used in the present invention comprises 2-fold higher concentrations of amino acids and vitamins than a common culture medium in the art to provide energy for cellular metabolism and maintain cell activity. D-glucose, which is metabolized into lactic acid and plays a less important role as an energy source, is lower. The concentration of L-glutamine in the secondary culture medium which affects on the amount of ATP synthesis is fixed to 4 mM. Further, the secondary culture medium comprises 0.7 nM of zinc, 0.25 nM of iron, 0.4 nM of copper, and 0.5 nM of manganese as trace elements, and contains sodium bicarbonate and HEPES having pH buffering capability at concentrations of 40 M and 10 mM, respectively. The secondary culture medium of the present invention comprises calcium and magnesium as essential minerals for intercellular adhesion at final concentrations of 1.5 mM and 0.8 mM, respectively, and also contains 4,500 mg/l of sodium chloride to adjust the osmotic pressure to the range of 280 to 310 mOsm/kg.

In addition, the secondary culture medium of the present invention farther comprises 10 mg/l of transferrin as an iron source; 0.01 mg/l of sodium selenite as an inorganic salt; 10 µg/l of hydrocortisone, 10 mg/l of insulin and 0.2 weight % of albumin as a hormone; and 0.1 to 10,000 ng/ml of a growth factor. The growth factor employable in the present invention may include, but are not limited to, HGF (hepatocyte growth factor), VEGF (vascular endothelial growth factor), PDGF (platelet-derived growth factor), BMP (bone morphogenic protein) and so on. More preferably, the secondary culture medium comprises 20 ng/ml of HGF as a growth factor.

In case of using a serum containing medium for the cultivation of a hair follicle organ, the initial growth rate of hair follicle is high, but it tends to degenerate early and get infected of infection (Randall V A. et al., *J Investing Dermatol Symp Proc.* 8(1):39-45, 2003). However, since the secondary culture medium of the present invention does not contain any serum, there is no risk of infection, and therefore, it can be effectively used as a medium for culturing and storing a hair follicle organ.

Further, the secondary culture medium of the present invention can maintain constant pH, which is an important factor for cell culture, through the buffering interaction between the bicarbonate salt and the metabolite. Namely, since the secondary culture medium of the present invention has higher concentrations of amino acids than a common culture medium such as Williams' medium E, there is the possibility of increasing pH as the concentration of ammonia, the final metabolite of amino acids, increases. But, the added bicarbonate salt as a buffering agent maintains the medium's pH at the range of 7.2 to 7.5.

Copper sulfate in the secondary culture medium of the present invention suppresses apoptosis caused by radical ions through the action of superoxide dismutase (SOD) which is a copper dependent enzyme and antioxidant present in the hair follicle, and stimulates the synthesis of a natural growth factor and extracellular matrix by inhibiting both 5α-reductase-1 and -2 through the action of other copper dependent enzymes.

Further, zinc is: an essential mineral component for the activation of a zinc finger transcription factor.

The dermal papilla auto-aggregate prepared according to the present invention has a size (about 100-200 µm) similar to that of the natural dermal papilla, and shows a strong direct cell-cell interaction because it is prepared by using natural cell contact. Further, histological observations of a section of the aggregate with hematoxylin/eosin indicate that the cells are closely aggregated. In particular, since the aggregate does not require any external stimulation or a matrix for cell adhesion and proliferation, it can be mass produced. More produced such aggregates show high hair follicle inductive ability, which can be effectively used for the treatment of alopecia through cell transplantation and the in vitro study for the hair follicle characteristics.

The following Examples are intended to Her illustrate the present invention without limiting its scope.

PREPARATION EXAMPLE 1

Preparation of a Secondary Culture Medium

One liter of a medium containing a higher concentration of amino acids and vitamins than an existing common culture medium was prepared according to the following composition described in Tables 1a to 1d, and 10 mg/l of insulin, 10 mg/l of transferrin, 0.01 mg/l of sodium selenite, 10 µg/l of hydrocortisone, and 0.2 weight % of albumin (2 g/l) were added thereto, to prepare a secondary culture medium.

TABLE 1a

| Inorganic salts (mg/l) | |
|---|---|
| $CaCl_2$ | 165 |
| $CuSO_4 \cdot 5H_2O$ | 0.0001 |
| $Fe(NO_3) \cdot 9H_2O$ | 0.0001 |
| KCl | 330 |
| $KNO_3$ | 0.076 |
| $MgSO_4$ | 98 |
| $MnCl_2 \cdot 4H_2O$ | 0.0001 |
| NaCl | 4800 |
| $NaHCO_3$ | 3360 |
| $Na_2HPO_4$ | 111 |
| $ZnSO_4 \cdot 7H_2O$ | 0.0002 |

TABLE 1b

| Other ingredients (mg/l) | | Other ingredients (mg/l) | |
|---|---|---|---|
| D-glucose | 2000 | HEPES | 2383 |
| Sodium pyruvate | 110 | Phenol red | 15 |

TABLE 1c

| Amino acids (mg/l) | |
|---|---|
| L-alanine | 50 |
| L-arginine | 100 |
| L-asparagine | 50 |
| L-aspartic acid | 60 |
| L-cystine•2HCl | 182.4 |
| L-glutamic acid | 150 |
| L-glutamine | 584 |
| L-glycine | 60 |
| L-histidine | 62.1 |
| L-isoleucine | 210 |
| L-leucine | 210 |
| L-lycine•HCl | 292 |
| L-methionine | 60 |

TABLE 1c-continued

| Amino acids (mg/l) | |
| --- | --- |
| L-phenylalanine | 132 |
| L-proline | 80 |
| L-serine | 84 |
| L-threonine | 190 |
| L-tryptophan | 32 |
| L-tyrosine | 208 |
| L-valine | 188 |

TABLE 1e

| Vitamins (mg/l) | | Vitamins (mg/l) | |
| --- | --- | --- | --- |
| Biotin | 0.026 | Niacinamide | 8 |
| D-Ca pantothenate | 0.026 | Pyridoxine•HCl | 8 |
| Choline chloride | 8 | Riboflavin | 0.8 |
| Folic acid | 16 | Thiamine•HCl | 3 |
| i-inositol | 14.40 | Vitamin $B_{12}$ | 0.026 |

EXAMPLE 1

Isolation of Hair Follicles

Figure 2:
FIG. 2: the procedure for isolating the fully matured hair follicle at a growth period from a mammal's skin.
Figure 2:
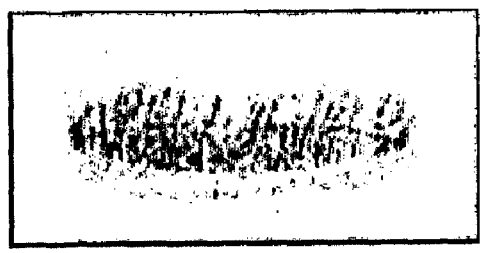
Figure 2:
Figure 2:
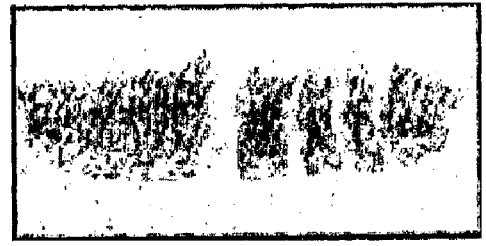
Figure 2:
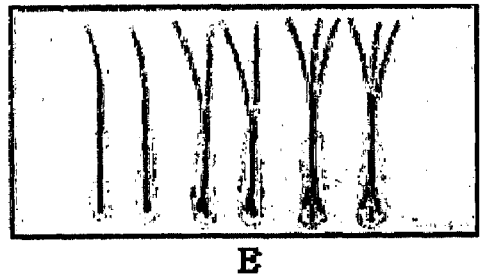
Figure 2:
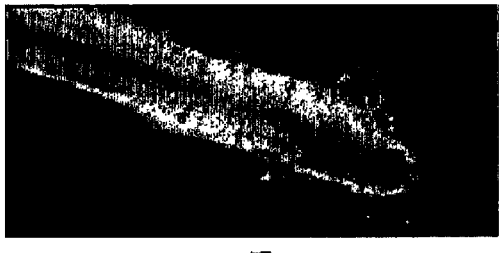

Hair follicles were obtained from the vibrissa hair of a Sprague-Dawley rat by a surgical operation. The separated vibrissa hair was stored at a tube filled with a common culture medium for the hair follicle, Williams' medium E (Gibco BRL, N.Y., U.S.A.). After the skin containing hair follicles was washed with a PBS solution containing penicillin G (10 units/ml), streptomycin (10 µg/ml) and amphotericin B (25 µmg/ml), peripheral adipose and dermal tissues were removed therefrom by using a knife, to separate the hair follicles. The hair follicle having the maximum anagen hair was selected from the separated hair follicles with an optical microscope. At this time, the judgment on a growth period of the hair follicle was determined by observing the hair bulb's structure. Peripheral adipose and dermal tissues were removed from the separated anagen hair follicle through a micromanipulation using a needle of a 1 cc syringe, to separate only the complete anagen hair follicle (FIG. 2).

EXAMPLE 2

Separation and Primary Culture of Dermal Papilla and Lower Dermal Sheath Cells

Figure 3:
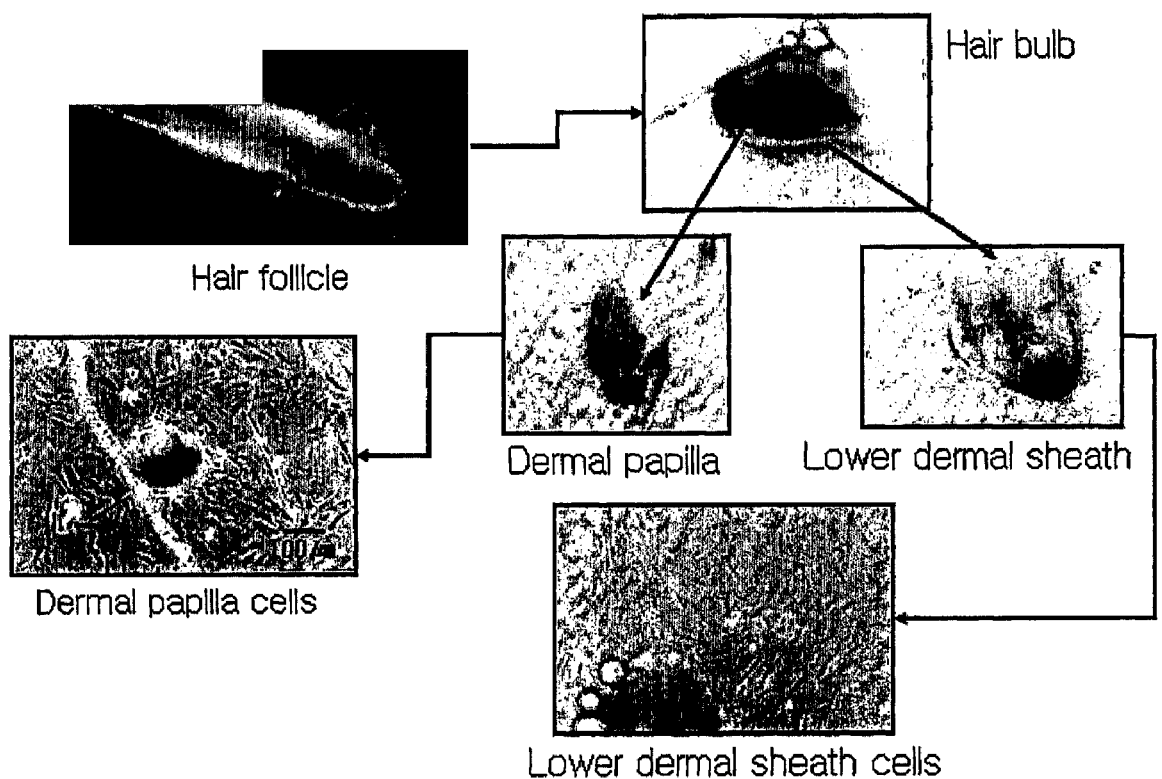
FIG. 3: the procedure for isolating dermal papilla and lower dermal sheath cells from the isolated hair follicle and culturing them in a primary culture medium.

In order to facilitate the adhesion of a dermal papilla tissue, 400 µl of fetal bovine serum (FBS) was added to a 35 mm cell culture dish and the bottom of the dish was evenly wetted therewith. Subsequently, while watching the hair bulb tissue present at the lower part of the separated hair follicle with an optical microscope, the dermal papilla within the tissue was detached therefrom using a syringe needle and the lower dermal sheath encompassing around the dermal papilla was separated. Each of the separated dermal papilla and lower dermal sheath was placed onto the culture dish wetted with FBS, and kept at a 37° C. incubator. When each of the separated tissues was adhered to the bottom of the culture dish, DMEM (Dulbecco's Modified Eagle Medium; Gibco BRL) as a primary culture medium was added thereto. At this time, for the purpose of enhancing adhesiveness of the tissue, the final concentration of FBS was adjusted to 20% with considering the amount of FBS initially added. The medium was carefully added to the culture dish and not replaced with a fresh one until the cells flow out from the tissue. When the cells began to flow out, the medium was replaced with DMEM supplemented with 10% FBS (FIG. 3).

EXAMPLE 3

Preparation of a Dermal Papilla Tissue

Figure 4:
FIG. 4: photographs of the primary cultured dermal papilla and lower dermal sheath cells when serially sub-cultured.
Figure 4:

The primary cultured dermal papilla and lower dermal sheath cells were continuously cultured in DMEM supplemented with 10% FBS (FIG. 4). When the cells were cultured up to more than 5 to 6 passage numbers that the dermal papilla and lower dermal sheath cells almost lost their hair follicle inductive ability, the cells were subjected to a monolayer culture until the cells reach to about 90% of the culture dish (A of FIG. 5). After then, in order to induce the differentiation for cell aggregation, the culture medium was replaced with a secondary culture medium which is a serum-free high concentration medium prepared in Preparation Example 1, and 20 ng/ml of HGF (rhHGF, R&D system) was added thereto (B of FIG. 5). The medium was replaced with a fresh one at about 5-day intervals. Cell aggregation began to appear from about 4 weeks after the cultivation (C of FIG. 5), and the cell mass being completely aggregated was spontaneously suspended into the medium from the culture dish (D and E of FIG. 5). From the point of beginning to suspend the cell aggregate, each time the medium was replaced, the waste medium was collected from the previous culture and subjected to centrifugation at 500 rpm for 3 min to recover cell aggregates. The cell aggregates were re-suspended in a fresh medium and kept at a culture container to maintain their culturing state until they are used in the following experiment.

Figure 5:
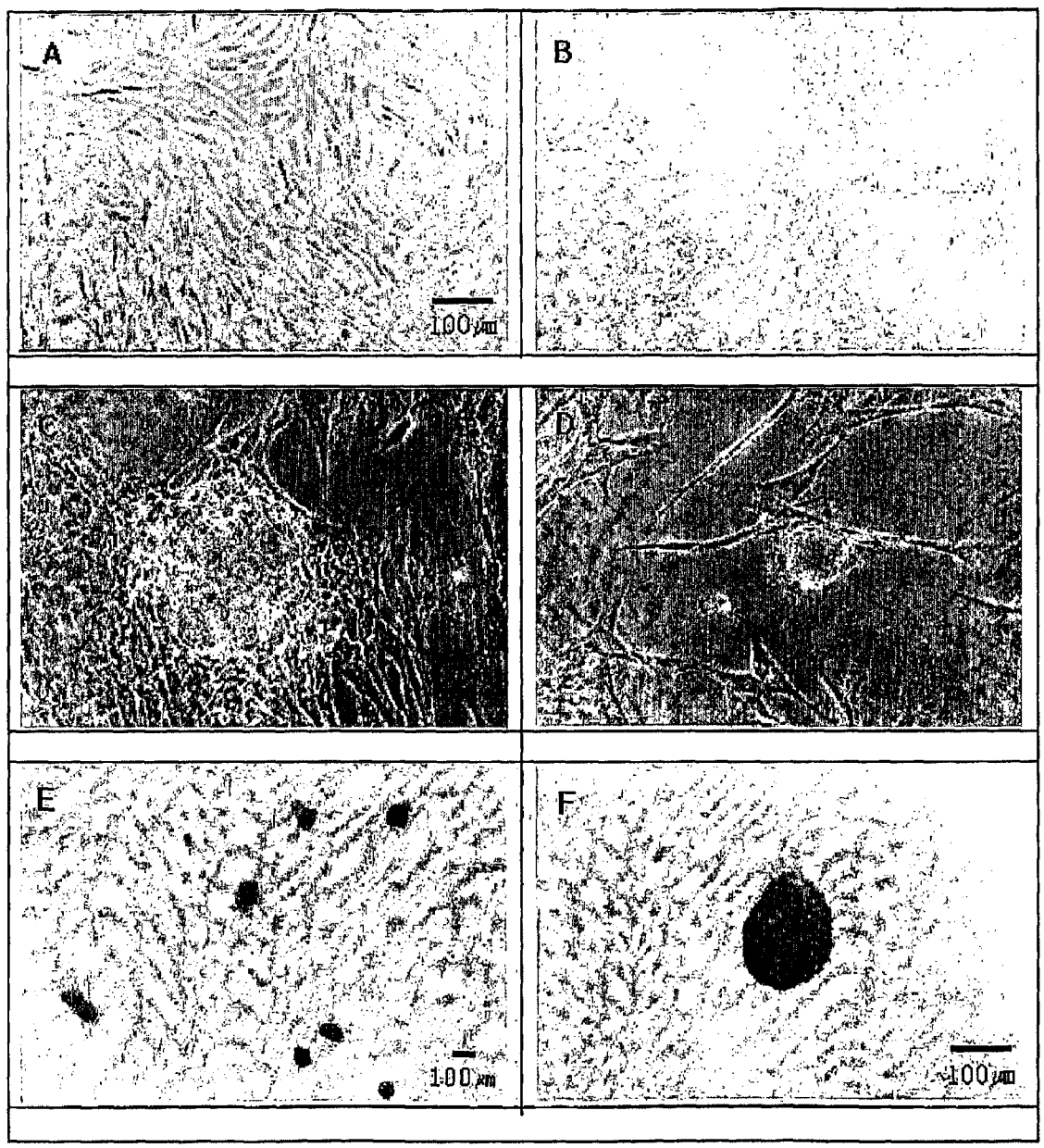
FIG. 5: photographs showing the procedure of forming cell aggregates by inducing auto-aggregation of the cultured dermal papilla cells, wherein A shows hair follicle dermal forming cells (dermal papilla and lower dermal sheath) cultured at 90% or more in a culture dish; B, the cells cultured for more than 3 weeks after the medium is replaced with a medium for aggregation; C, the initiated stage of cell aggregate formation by auto-aggregation; D, the aggregated cells prior to detaching from the culture dish to be suspended in the culture medium after the aggregation is almost completed; E, a plurality of cell aggregates simultaneously formed at several places within the culture dish; and F., a section of the cell aggregate histologically stained with hematoxylin/eosin.

As can be seen in D and E of FIG. 5, the dermal papilla auto-aggregate prepared according to the method of the present invention is similar in size (about 100-200 µm) to the natural dermal papilla and shows a strong direct intercellular interaction.

TEST EXAMPLE 1

Confirmation of Agglutinability of a Dermal Papilla Tissue

In order to confirm agglutinability of the dermal papilla tissue prepared according to the method described in Examples 1 to 3, its contact section was observed with a hematoxylin/eosin histological staining method.

As a result, as shown in F of FIG. 5, it has been found that the cells are is minutely aggregated, and thus formed aggregates show high solidity that are not easily destructed by an external stimulation.

COMPARATIVE EXAMPLE 1

Formation of Hair Follicles by Using a Natural Dermal Papilla Tissue

Figure 6:
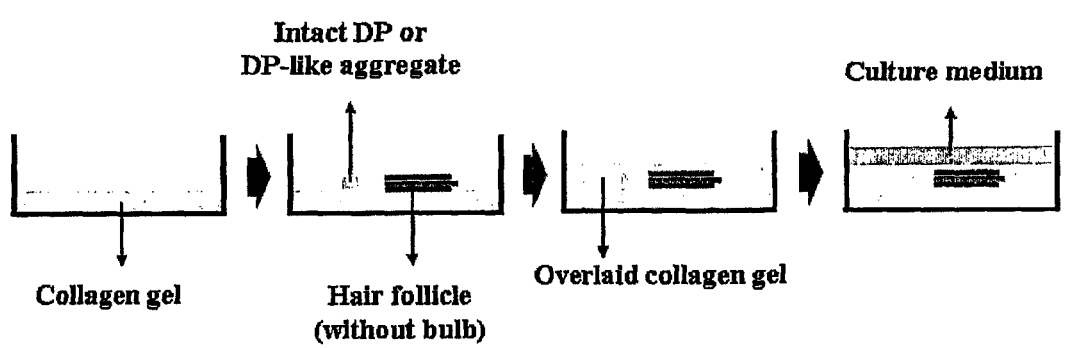
FIG. 6: the procedure for observing the interaction between the hair bulb and hair follicle in Comparative Example 1 and Test Example 2.
Figure 7:
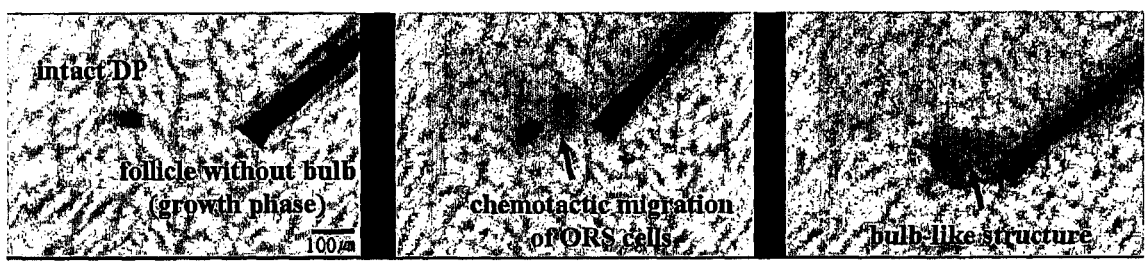
FIG. 7: photographs showing the procedure for in vitro formation of a new hair bulb structure through the interaction between the hair follicle lacking dermal papilla and hair bulb when these two tissues are co-cultured in a collagen gel matrix leaving some distance therebetween.

As described in FIG. 6, each well of a 24-well plate was filled with about 700 µM of a collagen solution and kept in a 37° C. incubator for 1 hr to induce gelation. The dermal papilla and hair follicle lacking hair bulb prepared in Example 2 were placed on the collagen gel leaving an interval of 300 µm between them and cultured for 5 to 10 min to attach to the gel surface. After 700 µl of the collagen solution was poured thereon once again and subjected to gelation, a K-SFM culture medium (Gibco BRL, N.Y., U.S.A.) was added thereto. About 1 week after that, outer root sheath cells were induced and encompassed around the dermal papilla. It was observed that the number of the outer root sheath cells were increased enough to form a hair bulb structure after about 15 days (FIG. 7).

COMPARATIVE EXAMPLE 2

Formation of Hair Follicles by Using an Artificial Dermal Papilla Tissue

In order to confirm whether the dermal papilla tissue prepared in Example 3 can actually induce the formation of the hair follicle, the experiment was conducted according to the same method as described in Comparative Example 1 except that the dermal papilla tissue of Example 3 was employed instead of a natural dermal papilla tissue.

Figure 8:
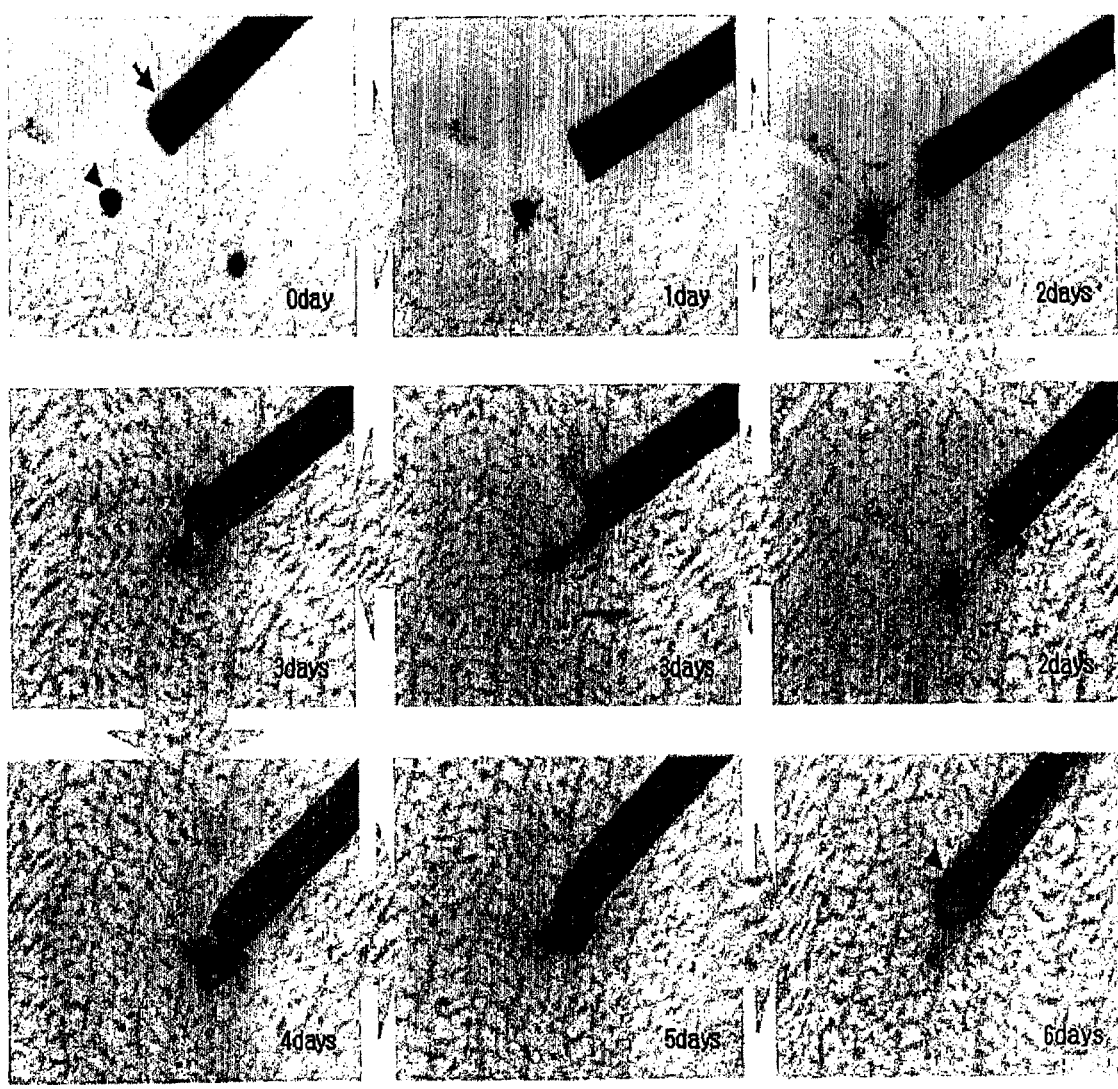
FIG. 8: photographs showing the procedure for in vitro formation of a new hair bulb (the head of an arrow) 6 days after hair follicle dermal-forming cells are cultured and the tissue (the head of an arrow) prepared by inducing cell auto-aggregation is co-cultured with the hair follicle lacking hair bulb (an arrow).

As a result, it was observed that the cells began to flow out from the hair follicle by the interaction between the dermal papilla tissue prepared in the present invention and the hair follicle cells lacking hair bulb, and formed a new hair bulb-like structure after about 1 week (FIG. 8).

Accordingly, it has been found that the dermal papilla tissue prepared according to the present invention has the same hair follicle inductive ability as a natural dermal papilla tissue.

While the invention has been described with respect to the above specific embodiments, it should be recognized that various modifications and changes may be made to the invention by those skilled in the art which also fall within the scope of the invention as defined by the appended claims.

What is claimed is:

1. A method for the preparation of a dermal papilla tissue which comprises the steps of:
   1) isolating dermal papilla and lower dermal sheath cells from the hair follicle;
   2) culturing the isolated cells in a medium selected from the group consisting of DMEM (Dulbecco's Modified Eagle Medium), DMEM/F-12, F-12, McCoy's 5A, RPMI 1640, Williams' medium E and IMDM (Iscove's Modified Dulbecco's Medium) medium; and
   3) inducing auto-aggregation of the cells obtained in step (2) by culturing them in a medium containing 30 to 200 mg/l each of L-arginine, L-asparagine, L-aspartic acid, L-cystine-2HCl, L-isoleucine, L-Leucine, and L-lysine; 30 to 210 mg/l each of L-phenylalanine, L-tryptophan, and L-tyrosine; 50 to 600 mg/l each of L-alanine, L-glutamic acid, L-glycine, L-histidine, L-methionine, L-proline, L-serine, L-threonine, and L-valine; 0.01 to 2 mg/l each of biotin, D-Ca pantothenate and riboflavin; 3 to 16 mg/l each of choline chloride, folic acid, niacinamide, pyridoxine-HCl, and thiamine-HCl; 10 to 15 mg/l of i-inositol; 0.02 to 0.03 mg/l vitamin $B_{12}$; 400 to 600 mg/l of glutamine; 1,500 to 3,000 mg/l of D-glucose; 3,000 to 3,500 mg/l of sodium bicarbonate ($NaHCO_3$); 2,000 to 2,500 mg/l of HEPES (N-[2-hydroxyethyl]piperazine-N'-[2-ethanesulfonic acid]); 1.0 to 2.0 mM of Ca; 0.5 to 1.0 mM of Mg; 0.25 to 0.7 nM each of Cu, Fe, Mn, and Zn; 4,000 to 5,000 mg/l of sodium chloride and 0.1 to 10,000 ng/ml of a growth factor selected from the group consisting of hepatocyte growth factor (HGF), vascular endothelial growth factor (VEGF), platelet-derived growth factor (PDGF), bone morphogenic protein (BMP).

2. The method of claim 1, which further comprises the steps of harvesting the auto-aggregated cells obtained in step (3) and culturing them in the medium of step (3).

3. The method of claim 1, wherein the cells are cultured in step (2) up to 5 to 6 passage numbers.

4. The method of claim 1, wherein the medium in step (3) further comprises hydrocortisone, insulin, transferrin, sodium selenite and albumin.

5. The method of claim 1, wherein the dermal papilla tissue is an aggregate consisting of dermal papilla and lower dermal sheath cells.

6. The method of claim 1, wherein said growth factor is HGF.

7. The method of claim 1, wherein the medium in step (2) is DMEM.

* * * * *